United States Patent [19]
Freed et al.

[11] Patent Number: 6,048,353
[45] Date of Patent: Apr. 11, 2000

[54] TREPHINE DEVICE FOR LOCATING AND CUTTING A CYLINDRICAL OR REVERSE TAPERED APERTURE IN FLEXIBLE MATERIAL

[75] Inventors: Paul S. Freed, Bloomfield Hills; Adrian Kantrowitz, Auburn Hills, both of Mich.; Seymour Mermelstein, Newton, Mass.

[73] Assignee: L. Vad Technology, Inc., Detroit, Mich.

[21] Appl. No.: 09/262,192

[22] Filed: Mar. 4, 1999

[51] Int. Cl.$^7$ .................................................. A61B 17/14
[52] U.S. Cl. ............................................ 606/184; 606/180
[58] Field of Search ..................................... 606/184, 180, 606/166; 600/566, 567

[56] References Cited

U.S. PATENT DOCUMENTS

3,058,471  10/1962  Shope ........................................ 128/305
3,701,352  10/1972  Bosworth ................................... 128/305

*Primary Examiner*—Michael Buiz
*Assistant Examiner*—Anthony S. King
*Attorney, Agent, or Firm*—Young & Basile, P.C.

[57] ABSTRACT

A trephine device for preparing apertures through a flexible material, such as skin of a patient, including a base plate having an upper surface and an opposed lower surface, where the upper surface has at least one upwardly protruding skin deforming contoured surface. The base plate is adapted to be removably inserted into a pocket surgically prepared in tissue of the patient. The device can include a handle member mounted on and projecting upwardly from the upper surface of the base plate. A clamping member is connected to the trephine device in overlying relationship to the upper surface of the base plate. The clamping member facilitates deformable, clamping, sandwiched engagement of the flexible material between the upper surface of the base plate and the clamping member. When the base plate is inserted into the pocket surgically prepared in the tissue of the patient, the skin of the patient is engageable between the base plate and the clamping member. The trephine device includes a cutter positionable relative to the handle member. The cutter is movable relative to the clamping member into cutting engagement with the flexible material deformably engaged by the clamping member to form an aperture having a cylindrical wall or a reverse tapered wall in the flexible material.

20 Claims, 4 Drawing Sheets

TREPHINE DEVICE FOR LOCATING AND CUTTING A CYLINDRICAL OR REVERSE TAPERED APERTURE IN FLEXIBLE MATERIAL

FIELD OF THE INVENTION

The present invention is directed to a tool employed to cut a circular opening of a specified diameter through a flexible material, membrane, or skin, and more particularly, the present invention is directed to a tool capable of producing a reverse-taper opening in a flexible material, membrane or skin, such as a surgical tool for forming a reverse-taper aperture in the skin of a patient in connection with implanting a medical device, such as a percutaneous access device, in the patient.

BACKGROUND OF THE INVENTION

Various instruments or devices can be implanted in a patient's body and require through-the-skin connection between the implanted device and an external device or instrument. A percutaneous access device (PAD) can be employed to provide such connection. A PAD is employed on a long-term or permanent basis to provide external pneumatic and electrical connection for implanted devices such as a cardiac assist device of the type described in U.S. Pat. No. 4,630,597. Percutaneous access devices of this general type are disclosed in U.S. Pat. Nos. 4,634,422 and 5,242,415, and consist basically of a body having a circular flange implantable beneath the patient's skin and a projection projecting coaxially along one side of the flange through the patient's skin. Electrical and/or pneumatic leads from within the patient's body pass through a passage in the projection of the PAD to a point where the electrical and/or pneumatic leads are accessible from the exterior of the patient's body.

As set forth in greater detail in U.S. Pat. No. 4,634,422, in order to implant the PAD, at some stage during the implantation procedure, it is necessary to cut a circular opening through the patient's skin to provide a passage for the projection. The epidermis, the outer layer of skin, has a natural propensity to attempt to close this surgical opening. U.S. Pat. No. 4,634,422 describes in detail a technique for firmly bonding the underlying dermal layer of skin to the sidewall of the projection to prevent the downgrowth of epidermis around the implanted device.

The formation of a bond between the dermis and the projection of the PAD is a delicate and time consuming operation which, as might be expected, requires a precise and uniform initial "fit" between the edge of the circular opening cut through the dermis and the outer periphery of the projection of the PAD. The diameter of the opening through the dermis is, ideally, closely matched to the outer diameter of the projection by the selection of a trephine of appropriate size to cut the opening through the skin.

However, due to the resilience of the skin, conventional trephines do not cut an opening with truly cylindrical sidewalls. Instead, the trephine produces an opening of a frusto-conical configuration with the larger diameter end of the opening facing outwardly of the skin. The outer sidewall of a PAD projection or analogous device is typically cylindrical or tapered with the larger diameter next to the inside of the skin. Because of this, the "fit" between the projection of the PAD and the dermis is loose in an area where it has the greatest need to be tight. This greatly increases the possibility of delayed or inadequate bonding between the skin layer and the projection, as well as increasing the risk of development of infection.

In U.S. Pat. No. 5,139,508 to Kantrowitz et al., a surgical tool for forming a circular opening through the skin having a diameter which increases with depth from the exterior surface of the skin is proposed. The device disclosed in Kantrowitz '508 is directed to a trephine with a cutting blade which is inserted into a pocket surgically formed beneath the skin. A rod member is inserted through the skin and threaded into the trephine. The rod member is attached to a spring biased plunger within a tool housing. Upon release of the plunger, the spring drives the plunger so as to drive the cutting edge of the trephine outwardly through the skin. This device produces the desired reverse taper opening. however, it is also desirable to control the taper angle with a greater degree of precision than that routinely obtainable with the device described in Kantrowitz '508. Additionally, this device requires assembly during surgery thus prolonging the procedure. Also there is a risk of parts being lost in the body.

It would be desirable to provide a trephine device which can produce the desired reverse taper holes by cutting conveniently from the outside. It is further desired that the device require little or no assembly and/or disassembly during surgery. Furthermore, it is desirable that the device permit the taper angle to be customized from application to application such that an angle of essentially zero or a near perpendicular cut may also be obtainable. Finally, it is desirable that the trephine device produce minimal tissue trauma and assist in the preparation of a subcutaneous pocket suitable for receiving the desired implant device, wherein the aperture placement is specifically oriented relative to the pocket thereby permitting easy and rapid installation of the implant after the reverse taper hole has been produced.

SUMMARY OF THE INVENTION

The invention is envisioned to include an apparatus and method for forming a cylindrical aperture or reverse tapered aperture in a flexible material. In this respect, the present invention encompasses a trephine device for forming at least one aperture in a flexible material of predetermined thickness, where the device includes an anvil having a frusto-conical surface for engaging one side of the flexible material, a reciprocal clamping member for engaging an opposite side of the flexible material from the anvil and for stretching the flexible material over the anvil into engagement with the frusto-conical surface of the anvil, and a reciprocal, cylindrical cutter disposed coaxial with the anvil and having a cutting edge engagable with the flexible material held in a stretched condition by the clamping member for cutting through the flexible material to the anvil for forming an aperture through the flexible material. Preferably, the clamping member is moveable independently of the cutter. The frusto-conical surface of the anvil defines an axis and forms an angle with respect to the axis selected to form a cylindrical aperture through the flexible material when the stretched material is cut with the cutter. By selecting an appropriate angle, the anvil and cutter can cooperate to produce a cylindrical aperture or a reverse tapered aperture through the flexible material when the material stretched over the anvil is cut with the cutter.

The present invention includes a method for forming at least one aperture through a flexible material of predetermined thickness including the steps of: operably engaging one side of the flexible material with an anvil having a frusto-conical surface; operably engaging an opposite side of the flexible material from the anvil with a moveable clamping member for stretching the flexible material over the anvil into engagement with the frusto-conical surface of the anvil; and moving a cylindrical cutter in coaxial relationship with the anvil, the cutter having a cutting edge engagable with the flexible material held in a stretched condition by the clamping member for cutting through the flexible material to the anvil thereby forming an aperture through the flexible material. The method can also include the step or steps of moving the clamping member independently of the cutter; and/or forming a circular aperture or reverse tapered aperture as the cutter passes through the flexible material stretched over the anvil. The method can include the step or steps of reciprocating the cutter when disposed coaxial with respect to the anvil; and/or rotating the cylindrical cutter about an axis coaxial with the anvil as the cutter passes through the flexible material stretched over the anvil.

The present invention is an integrated trephine device for producing reverse taper apertures through a flexible material, membrane, or skin. The trephine device according to the present invention includes a base plate having opposed upper and lower surfaces with at least one upwardly protruding material-deforming contour defined in the upper surface, and a handle member releasibly mounted on the base plate and projecting upwardly from the upper surface. A material-clamping mechanism is movably connected to the trephine device in overlying relationship to the upper surface of the base plate so as to facilitate clamping engagement of the flexible material sandwiched between the upper surface of the base plate and the material-clamping mechanism. A cutter mechanism is movably positioned in the handle member so as to be movable relative to the material-clamping mechanism in a direction essentially perpendicular to the base plate.

The present invention is also directed to a method for employing the trephine device comprising the steps of inserting the base plate of the trephine device into contact with the flexible material, membrane, or skin; positioning the material-clamping mechanism into engaging contact such that the material is deformably positioned over an anvil protruding upward from the base; and depressing the cutter mechanism through the material into contact with the upwardly protruding anvil.

Preferably, the present invention is an integrated trephine device for producing reverse taper apertures through the skin and includes a base plate having opposed upper and lower surfaces with at least one upwardly protruding skin deforming contour defined in the upper surface, and a handle member releasibly mounted on the base plate and projecting upwardly from the upper surface. A skin clamping mechanism is movably connected to the trephine device in overlying relationship to the upper surface of the base plate so as to facilitate clamping engagement of the skin sandwiched between the upper surface of the base plate and the skin clamping mechanism when the base plate is inserted into a pocket surgically prepared in the tissue of the patient. A cutter mechanism is movably positioned in the handle member so as to be movable relative to the skin clamping mechanism in a direction essentially perpendicular to the base plate.

Preferably, the present invention is also directed to a method for employing the trephine device comprising the steps of preparing a pocket beneath a patients' skin; inserting the base plate of the trephine device into the prepared pocket; positioning the skin clamping mechanism into engaging contact such that the skin is deformably positioned over an anvil protruding upward from the base; and depressing the cutter mechanism through the skin into contact with the upwardly protruding anvil.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

For a more complete understanding of the nature and objects of the invention, reference is directed to the following detailed description and drawing in which like reference numerals are used throughout the various drawing figures and wherein.

BRIEF DESCRIPTION OF THE PREFERRED EMBODIMENT

The surgical trephine device 10 of the present invention includes a handle member 12 releasibly mounted on a base plate 14. The base plate 14 is adapted to be removably insertable into a pocket surgically prepared in the tissue of the patient. The handle member 12 is connected to the base plate 14 by suitable mounting means 16, such as the handle bolt 18 extending perpendicularly upward through base 14 and through a suitably defined bolt aperture 20. The handle bolt 18 terminates in a handle bolt lock nut 22.

The surgical trephine device 10 of the present invention also includes a skin clamping mechanism 23 movably connected to the trephine device 10 so as to facilitate insertion of the base plate 14 into the prepared surgical pocket and clamping engagement of the skin (see FIGS. 3–5) sandwiched between the base plate 14 and the skin clamping mechanism 23 during actual creation of the surgical aperture.

Figure 3:
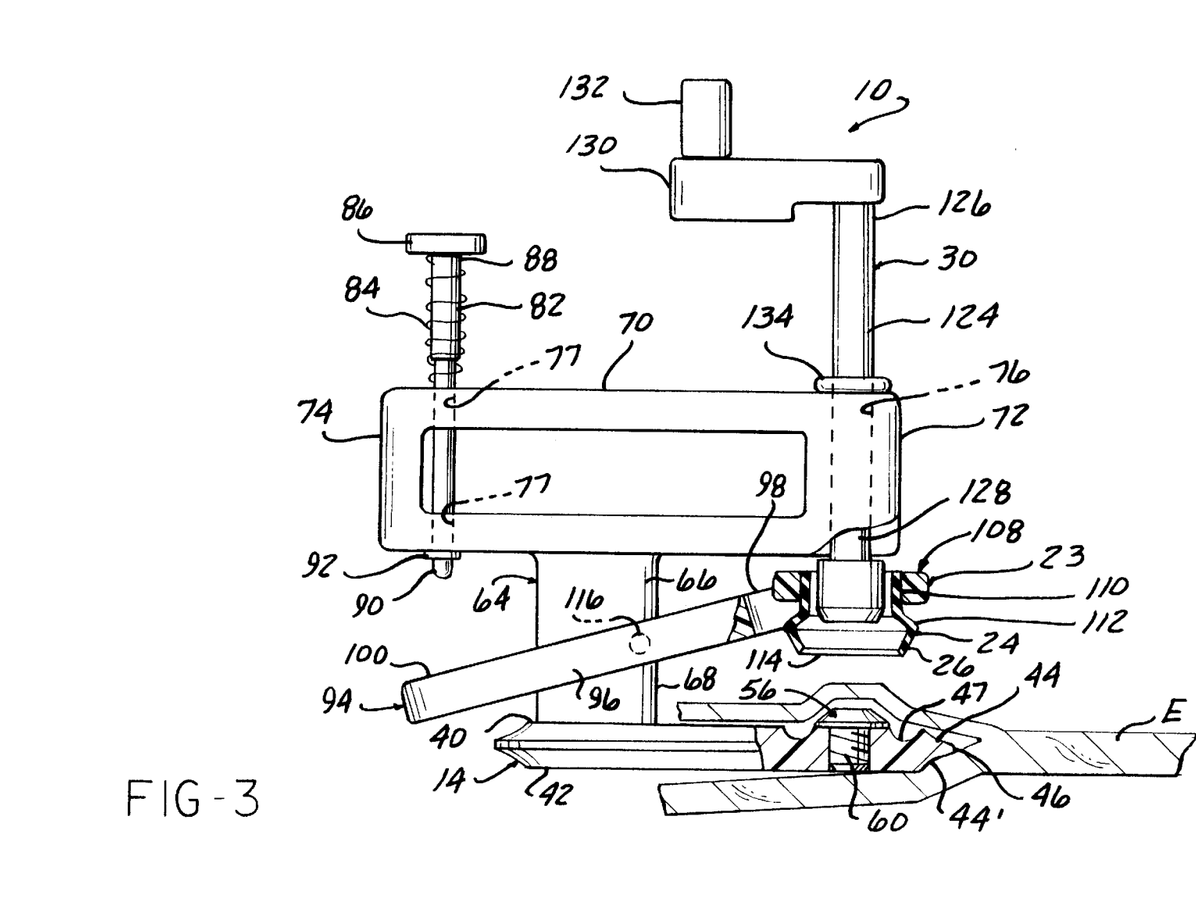
FIG. 3 is a partial cross sectional view of the device shown in FIG. 1 the ready position.
Figure 4:
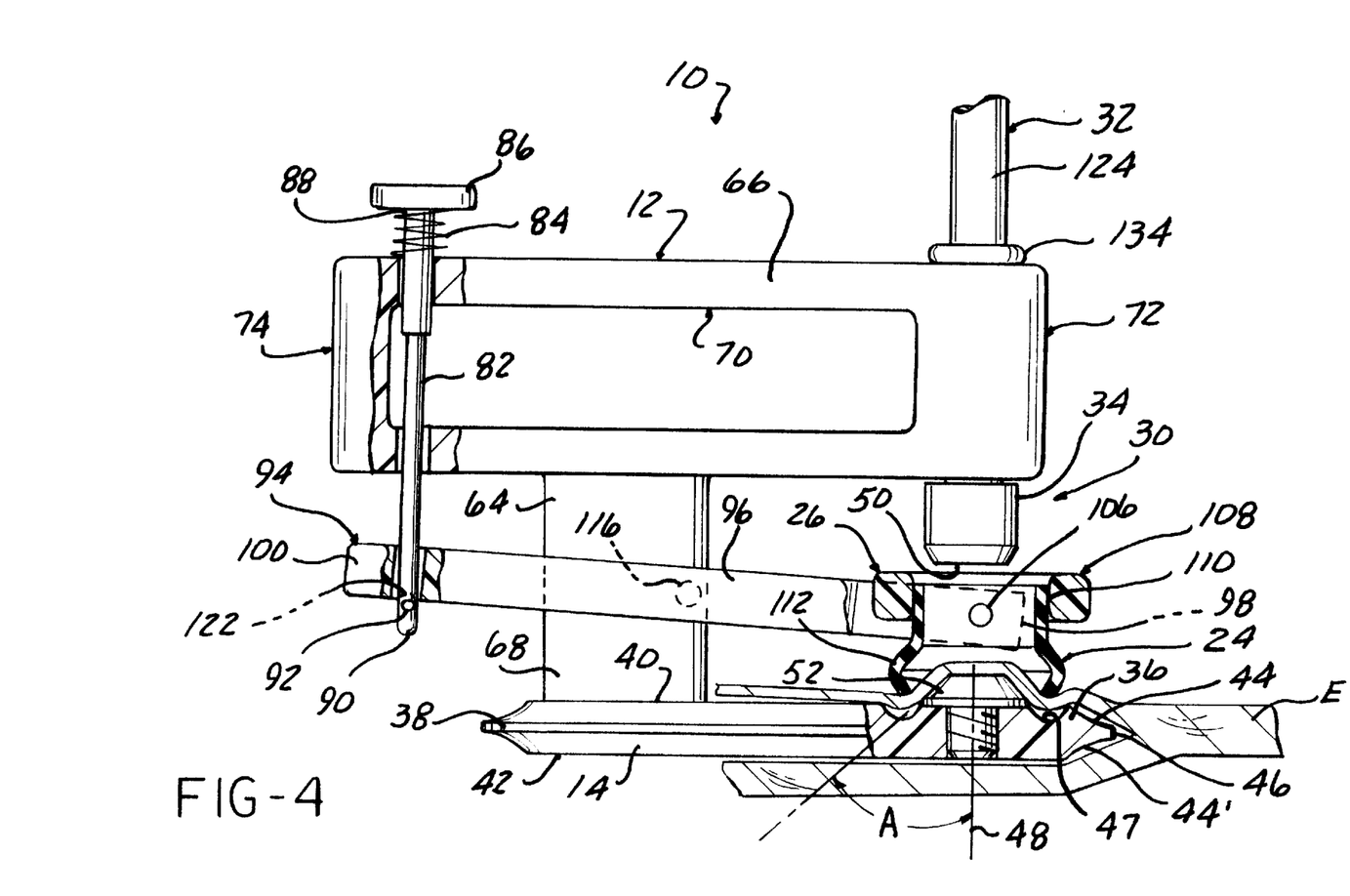
FIG. 4 is a partial cross sectional view of the tool of the present invention with the clamp arm in the compressive position.

The skin clamping mechanism 23 includes suitable means 24 for releasibly engaging the outer surface of a skin layer E shown in FIGS. 3 and 4. The engaging means 24 releasibly engages the skin layer E in FIG. 5 and, preferably, includes a circular deflection member, such as skin engaging unit 26. Skin engaging unit 26 is shown in greater detail in FIG. 5 and, preferably, includes a tubular element 28 defining a hollow central interior aperture for compressively deforming a layer of skin E against contours defined in the underlying base plate 14.

A cutter mechanism 30 is positioned in the handle member 12 so as to be telescopically movable into and out of the skin engaging unit 26 in a direction essentially perpendicular to the base plate 14. Preferably, the cutter mechanism 30 is also rotatable coaxially about a center axis defined by the skin engaging unit 26. In the preferred embodiment, the cutter mechanism 30 includes means 32 for retractably extending a tubular cutter element 34 into contact and through skin layer E located within the space defined by skin engaging unit 26.

In the trephine device 10 of the present invention, the base plate 14 is generally an elongate body having a first region 36 adapted to be received within a pocket surgically prepared in the skin tissue of a patient and an opposed second region 38. The outer peripheral contours of the first region 36 may have any suitable geometric profile, but, preferably, are similar to the ultimate device to be implanted at the conclusion of the surgical procedure, such as a PAD or similar device.

Figure 1:
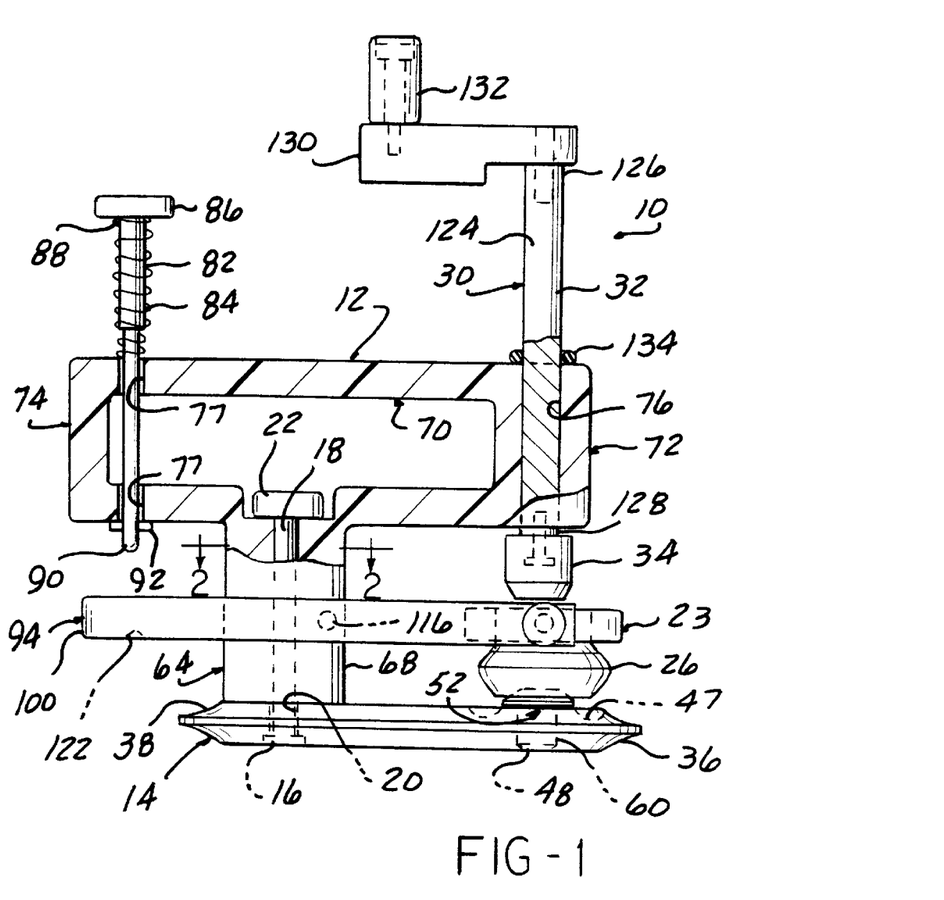
FIG. 1 is a partial cross sectional side view of the trephine device of the present invention.
Figure 2:
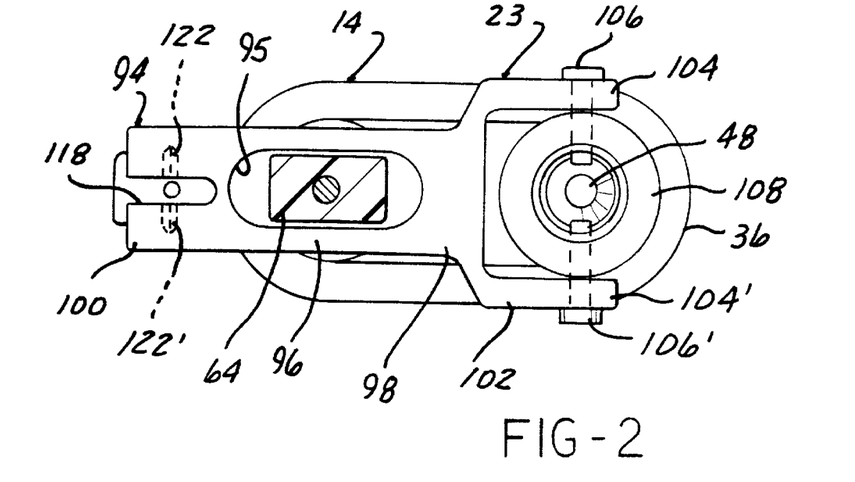
FIG. 2 is a cross sectional view of the trephine device taken through the 2—2 line in FIG. 1.

As illustrated in FIG. 2, the base plate 14 has essentially ellipsoidal upper and lower faces 40,42 with the first region 36, preferably, positioned in one forward axis 48 of the ellipsoidally shaped base plate 14. In the preferred embodiment, the base plate 14 has symmetrically concave surfaces 44,44' extending along and defining an outer lip 46 of the base plate 14.

The first region 36 of base plate 14 includes an upwardly oriented profile such as the essentially circular relief 47 and anvil 52 defined in the upper face 40. The circular relief 47 is, positioned at the desired location of trephining. In the preferred embodiment the circular relief 47 is located coaxial to the forward axis 48 projecting from the base plate through the cutter mechanism 30. In the preferred embodiment, an anvil 52 projects above the essentially planar surface of the upper face 40. In the preferred embodiment as shown, the anvil 52 has head element 54 composed of a frusto-conical upper region 56 integrally formed with a squat cylindrical base 58. The cylindrical base 58 of head element 54 has a maximum diameter essentially equal to or slightly less than the diameter of the inner surface of the circular relief 47 in base plate 14.

In the preferred embodiment, the frusto-conical upper region 56 of head element 54 has a taper sufficient to deform the skin layer E when it is positioned in overlying relationship thereto. Preferably, the angle of taper of the frusto-conical upper region 56 is between about 20° and about 40° with a taper being preferred.

In the preferred embodiment of this invention, the anvil 52 is removably positionable in the base plate 14. The anvil 52 includes an essentially cylindrical rod 60 formed integrally with and extending downwardly from squat cylindrical base 58 of the head element 54. The cylindrical anvil rod 60 is adapted to be matingly received within an aperture defined in the base plate 14. The aperture is coaxial with the essentially circular relief 47. The anvil 52 can be inserted in the aperture 62 so as to be removable from the base plate 14 and readily replaceable as desired.

In the preferred embodiment, the anvil 52 is constructed of a material having sufficient characteristics of deformability so as to be capable of withstanding scoring by a surgical cutting edge, as may occur during the actual trephining procedure, without causing appreciable dulling of the cutting blade. The material employed will also be one which will permit deformation of a suitably elastic material, such as skin, when that material is compressively stretched thereover. Finally, the material employed will be a material capable of being sterilized. Ideally the material of choice will be one capable of being used for a single procedure, removed from the base plate 14, and discarded. In the preferred embodiment, the anvil 52 is made of a polymeric material such as polypropylene. It has been found that polypropylene is capable of permitting depression and penetration of the cutting edge 50 of the cutter mechanism 30. The polypropylene material employed in the anvil can permit such penetration, as well as any recutting or touch-up of the cut employed in the skin layer E without materially dulling the cutting edge. The polypropylene material is both sterilizable and disposable and is, therefore, suitable for single use application. Other suitable materials would be readily known to the skilled artisan.

The handle member 12 is, preferably, composed of a handle pedestal 64 having an upper region 66 and an opposed lower region 68. The lower region 68 is preferably in contact with the upper face 40 of the base plate 14 such that the handle pedestal 64 projects upward from the upper surface 40 of the base plate 14 in an essentially perpendicular manner. In the preferred embodiment, the means 16 for releasibly mounting the handle member 12 to the base plate 14 is located in the handle pedestal 64. In the preferred embodiment, bolt aperture 20 extends through the handle pedestal 64 to receive the handle bolt 18.

The handle member 12 also has a hand grasp member 70 integrally connected to the upper region 66 of the handle pedestal 64. In the preferred embodiment, the hand grasp member 70 has a central opening defined therein sufficient to permit the handle member 12 to be grasped by the hand of the surgeon or other operating room personnel to assist in placement of the trephine device 10 in the manner to be described subsequently. As shown in the various drawing figures, the hand grasp member 70 has a first arm portion 72 and an opposed second arm portion 74. The first arm portion 72 extends perpendicularly outward from the handle pedestal 64 at an orientation essentially parallel to the base plate 14. The first arm portion terminates at a position in overlying relationship to the anvil 52. The second arm portion 74 of the hand grasp member 70 opposed to the first arm portion 72 extends to a position beyond the end of the second region 38 of base plate 14.

A first aperture 76 extends through the first arm portion 72 of the hand grasp member 70 from top to bottom. The first aperture 76 is located at a position essentially coaxial to the anvil 52 and the forward axis 48 located in base plate 14. Cutter mechanism 30 is retractably movable relative to the first aperture in a manner to be described subsequently. A second aperture 77 is located adjacent the second arm portion 74 of hand grasp member 70.

The hand grasp member 70 also includes means for releasibly anchoring the clamping mechanism in engagement with the skin overlying the base plate. A clamp rod 82 is retractably positioned in the second aperture 77. The clamp rod 82 is maintained in retracted position by a suitable biasing means, such as spring 84, for urging against the upper surface of the handle member, and is removably fastened to the clamp rod 82 between the upper surface and a suitable knob 86 located proximate to the upper end 88 of clamp rod 82. The lower or second end 90 of the clamp rod 82 projects through lower portion of the second aperture 77. A cross pin 92 is located proximate to the lower or second end 90 of the clamp rod 82. The trephine device 10 of the present invention also includes means for raising or lowering the skin clamping mechanism 23 relative to the base plate 14 as required during the trephining procedure. In the preferred embodiment, this is accomplished by the clamp rod 82 in the manner described subsequently.

In the preferred embodiment, the skin clamping mechanism 23 consists of a clamp arm 94 pivotally mounted on the handle member 12 at a suitable location on handle pedestal 64. As seen in top plan view in FIG. 2, the clamp arm 94 is composed of a central portion 96 having an essentially oval aperture adapted to receive the handle pedestal 64 there-through. The central portion has a first end 98 and a second end 100 opposed to the first end 98. A fork member 102 extends contiguously from the first end 98. The fork member 102 is composed of two arms 104, 104' through which traverse corresponding swivel bolts 106, 106'. In the preferred embodiment, the swivel bolts 106, 106' project inwardly through the respective sides of the arms 104, 104' into the interior of the fork member 102 at a location above and perpendicularly planar to the forward axis 48. Swivel bolts 106, 106' engage skin engaging unit 26 permitting the skin engaging unit 26 to pivot relative to arms 104, 104' of fork member 102.

As illustrated in the drawing figures, skin engaging unit 26 preferably comprises a tubular skin pad element 28 releasibly mounted to the interior annular surface of clamp ring 108. In the preferred embodiment, the tubular skin pad element 28 is composed of a flexible deformable material with sufficient deflection properties to deform the skin layer E to the contours of the underlying anvil 52 when the base plate 14 is in position in the manner described subsequently. Preferably, the material employed in the tubular skin pad element 28 is a sterile or sterilizable, flexible polymeric material such as polyvinyl chloride. The material employed in the tubular skin pad element 28 can be substituted by other material as would be readily known to the skilled artisan.

The tubular skin pad element 28 is configured to minimize trauma to the skin during the deflection process. In the preferred embodiment shown in FIGS. 1, 3, 4 and 5, the tubular skin pad element 28 is composed of an upper cylindrical region 110 engagable with the interior surface of clamp ring 108. The upper cylindrical region 110 is maintained in contact with the interior surface of the clamp ring 108 by any suitable means such as by interference fit or the like. The tubular skin pad element 28 has at least one bead 112 contiguous with the upper cylindrical region and positioned at a location extending outwardly lower than the clamp ring 108 and associated cylindrical region 110. A terminal end 114 of tubular skin pad element 28 forms a reverse tapered angular surface with the diametrically smallest region being located inward of the lowermost tip of the terminal end. The angular surface thus formed defines an angle that is essentially equal to the taper angle defined by the frusto-conical upper region 56 of anvil 52.

In the preferred embodiment, skin engaging unit 26 is detachable from the skin clamping mechanism 23. Preferably, the swivel bolts 106, 106' are retractable or removable from the apertures defined in arms 104, 104' to release the clamp ring 108. This permits ready removal and replacement of skin engaging unit 26 after each use.

The skin clamping mechanism 23 is removable from engagement with the handle pedestal 64 when the handle member 12 is disengaged from base plate 14. During operation, skin clamping mechanism 23 is pivotal about a pivot rod 116. Pivot rod 116 is positioned in the central portion 96 of the skin clamping mechanism 23 by collinear apertures projecting through the central portion 96 of the clamp arm 94 and through the handle pedestal 64 of the hand grasp member 70. Pivot rod 116 is oriented essentially perpendicular to the aperture 76 through the first arm portion 72 located in the handle member 12.

An elongate slot 118 projects inward from the second end 100 of the clamp arm 94. The elongate slot 118 is, preferably, an elongate opening extending perpendicularly through the clamp arm 94 from top to bottom and terminating at a region adjacent the central portion 96 prior to the aperture 95. The clamp arm includes a pair of coaxial grooves 122, 122' projecting perpendicularly outward from the elongated slot 118 located in the lower face. The pair of grooves project perpendicularly outward from the longitudinal axis defined by elongated slot 118.

The clamp rod 82 can be moved to a position where the cross pin 92 engages the bottom of the handle member 12 to allow free pivotal movement of the clamp arm and supported skin engaging unit 26 with respect to the anvil 52. The clamp rod 82 can be moved against the biasing force of the clamp spring 84 to engaging with the grooves 122, 122' in the clamp arm 94 to cause biased pivotal action of the releasible engaging means 24 toward the anvil 52. The cross pin 92 is located in the distal end of clamp rod 82 and can be rotated to pass through the slot 118 in order to bring the cross pin 92 into engagement with the grooves 122, 122' located in the second end 100 of clamp arm 94. The spring 84 causes compression of the skin engaging unit 26 against the upper surface of a skin layer acting through the clamp rod 82, when the cross pin 92 has been rotated into alignment with the grooves 122, 122' after passing through elongate slot 118 as the clamp rod is depressed against the forces of clamp spring 84. The clamp spring 84 will bias the clamp rod 82 and the second end 100 of the clamp arm 94 of the skin clamping mechanism 23 upward causing a corresponding downward movement of the first end 98 thereby depressing the skin engaging unit 26 against skin layer E. The swivel bolts 106, 106' allow the skin engaging unit 26 to remain aligned in coaxial relationship with the anvil 52 and cutter mechanism 30 as the clamp arm 94 rotates about the pivot rod 116 during clamping operations.

As previously indicated, cutter mechanism 30 includes a cutter rod 124 telescopically received and movable relative to aperture 76 defined in handle member 12. Cutter rod 124 has a first, upper end 126 and an opposite lower end 128. The cutter mechanism 30 also includes means for imparting rotational motion to the cutter rod 124 about a rotational axis of the cutter rod 124. As depicted in the drawing figures, the rotational motion imparting means may include a crank 130 and a crank handle 132.

The cutter rod 124 is axially slidable within the aperture 76 defined in the hand grasp member 70 to the axial location desired by the operator. The cutter rod 124 is maintained in position relative to the aperture 76 by a suitable retention means, such as a shaft friction ring 134 located in engagable contact with the outer cylindrical surface of the cutter rod 124 and the upper surface of handle member 12.

Figure 5:
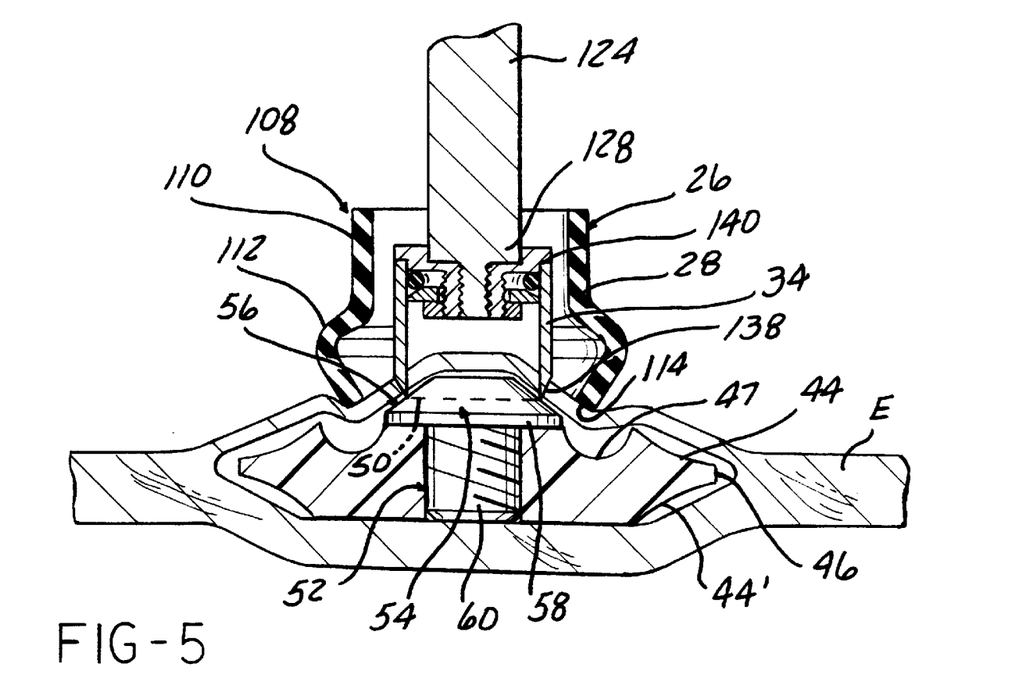
FIG. 5 is a detailed drawing showing the cutter chuck in the lower, material-engaging position as the cutter produces the reverse taper opening desired.
Figure 6:
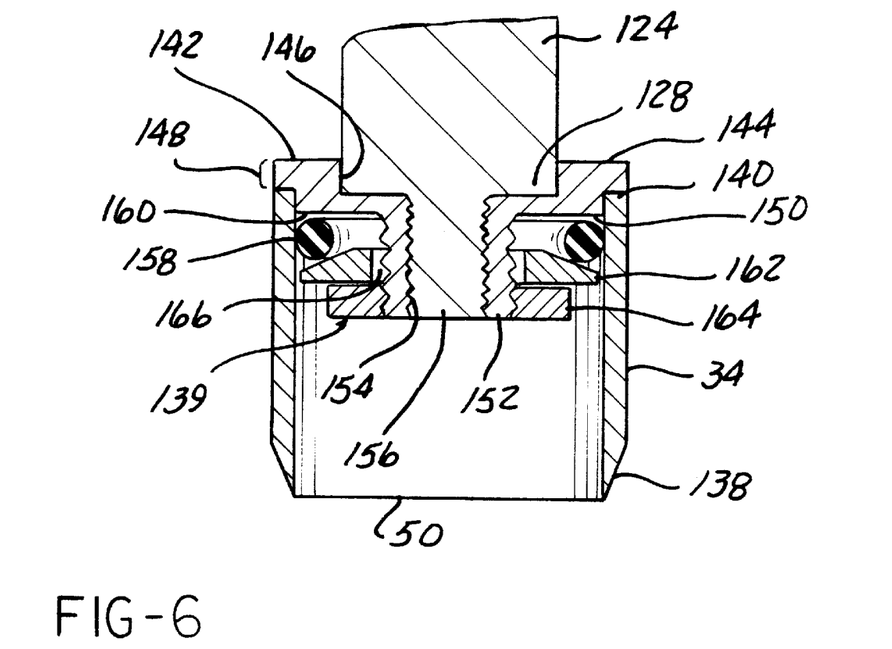
FIG. 6 is a detailed drawing of a cross sectional view of the shaft mounting chuck for the tubular cutter of the present invention.

The tubular cutter element or cutting blade 34 is removably mounted to the second end 128 of cutter rod 124. Cutting blade 34 and details of the preferred mounting assembly mechanism are depicted in FIGS. 5 and 6. In the preferred embodiment, the cutting blade 34 has a first cutting surface 138 located distal to the cutter rod 124. The cutting surface 138 is characterized by an outwardly oriented tapered edge such that the cutting edge 50 is located at the interior diameter of the tubular cutting blade 34. A mounting edge 140 is opposed to the cutting edge 50. In the preferred embodiment, the tubular cutting blade 34 is attached to a mounting hub 142. As depicted in FIG. 6, the mounting hub 142 has a first upper surface 144 adapted to contact the lowermost portion of cutter rod 124. A circular detent 146 is formed in the first surface 144 to receive and surround the terminal end 128 of the cutter rod 124. A flange member 148 extends outwardly radially from the first surface 144 of the mounting hub 142 and into abutting relationship with an axial end of the cutting blade 34 opposite from the cutting edge 50 to define a radially extending abutting joint.

A hub pilot body portion 150 is defined in the mounting hub 142 at a location opposed to the first surface 144. The hub pilot body portion 150 includes an inset cylindrical wall portion adapted to contact the interior surface of cutting blade 136 in the manner shown in FIG. 6. Mounting hub 142 also includes an axially extending projection 152 having internal and external threads formed on the cylindrical projection 152. The projection extends coaxially with respect to the mounting hub 142 at a location opposite from the first surface 144. The projection 152 has a central aperture 154 adapted to receive a suitable fastening member 156 projecting downwardly from the cutter rod 124.

A cutter chuck assembly 139 includes a compressible, deformable friction ring 158, preferably an O-ring composed of an elastomeric material such as Buna-N. When the tubular cutter element 34 is seated against the flange member 148, the friction ring 158 is positioned in frictional contact against the interior surface of the tubular cutting blade 34 and the interior surface 160 of the mounting hub 142. A locking member, such as wedge lock washer 162, is positioned axially around the projection 152 and in position for mating, compressive engagement against the friction ring 158. A lock nut 164 is tightened over the outer threads 166 of projection 152 to force the friction ring 158 to jam between the lock washer 162, the interior surface 160 of the mounting hub and the internal diameter of the tubular cutting blade 34. The frictional contact of the ring 158 locks the tubular cutter element 34 to the hub assembly. As can be appreciated, the cutter chuck assembly 139 can be readily stripped down for cleaning and sterilization by removal of the lock nut 164. In the preferred embodiment, all elements are composed of stainless steel which can be readily sterilized. The compressible O-ring 158 is composed of a material which can be gas sterilized and is considered disposable. In this way, the trephine device 10 of the present invention can be used with disposable tubular cutting blades 34.

The trephine device of the present invention can be employed in the following manner. The base 14 of trephine device 10 is inserted into a prepared subcutaneous pocket. The subcutaneous pocket is of sufficient dimension to receive the forward or leading region of base 14. The subcutaneous pocket is formed generally about 3 inches wide and about 3 inches deep. It is to be understood that the dimensions of the base plate 14 and the pocket can be varied to accommodate the device which is to be ultimately implanted. The skin is stretched over the tapered anvil 52 when placed under tension by actuation of the skin clamping mechanism 23 as previously described, and is held in position during the cutting procedure to produce the desired reverse taper aperture.

The trephine device 10 of the present invention is used by lifting the skin clamping mechanism 23 to permit clearance between the skin engaging unit 26. By grasping the handle 12 of the device, the surgeon can slide the base plate 14 into the subcutaneous pocket to the desired distance. When in the desired position, skin is positioned over the anvil 52 to define a site for cutting the aperture through the skin. The skin clamping mechanism 23 is then released, and the clamp rod 82 is engaged through the slot 118 in the clamp arm 94 and rotated so that the cross pin 92 operably engages with grooves 122, 122'. The compressed clamp spring 84 applies a fulcrum load to the skin pad via the skin engaging unit 26 which stretches and clamps the skin over the anvil 52. The skin engaging unit 26 is free to swivel via clamp ring 108 and, when in position, stretches and clamps the skin over the anvil 52. Circular relief 47 provided in base plate 14 permits the skin engaging unit 26 to sustain the skin in the stretched position without bottoming out. The skin engaging unit 26 is of sufficient dimension to ensure clearance of the anvil when in the clamped position illustrated in FIG. 5.

Handle member 12 can be grasped by one hand to steady the device 10 during cutting. The free hand is used to rotate and gently push down on the cutter mechanism 30 to drive cutter rod 124 rotatively and axially into cutting engagement with the skin as the cutting edge 50 travels toward the anvil 52. Cutting action is completed when the cutting blade 34 reaches the anvil 52. The anvil 52 can be cut slightly to ensure a complete cut through the skin to free any coupon of skin from the surrounding tissue. The separated skin typically is held inside the cutting blade 34 until the skin is removed or until the skin is disposed of in any suitable manner. In the preferred embodiment, the anvil 52 is made of a suitable material such as polypropylene which can be penetrated by the cutting blade. A suitable material for the anvil 52, such as polypropylene or the like, permits recutting or touch-up cutting without materially dulling the cutting blade 34. The trephine device 10 is removed by reversing the preceding procedure. The cutter rod 124 is held in the raised position illustrated in FIG. 3 by resetting the friction ring 134 in the desired position.

The trephine device 10 of the present invention permits installation of a new cutting blade 34 even without removal of the trephine from position when necessary. In order to accomplish this, the body of the cutting blade 34 is grasped and rotated counterclockwise to unscrew the cutter and chuck assembly. The replacement assembly can, then, be positioned. In the preferred embodiment, the cutter chuck assembly 139 is intended for use with disposable cutting blades 34.

The trephine device 10 of the present invention can be stripped down for cleaning by removing the handle lock nut 22, and then the handle 12 can be lifted from the base plate. The cutter chuck assembly 139 can be removed as discussed previously, and then the cutter rod 124 can be removed from the handle 12. The clamp rod 82 can be removed from the handle 12 by orienting lock pin 92 so that the lock pin 92 passes through slots (not shown) defined in the handle 12. The handle bolt 16 and anvil 52 can be removed from the base plate 14. The clamp arm 94 can slide off from the handle 12 after the pivot rod 116 is removed. The skin engaging unit 26 can be removed by disengaging swivel bolts 106, 106'. If desired, the skin engaging unit 26 can be discarded and replaced with a new unit.

Thus, in this manner, the trephine device of the present invention can be effectively used to prepare a reverse taper aperture with minimum trauma and a high degree of accuracy and precision. The trephine device of the present invention provides means for removing and replacing parts as required to insure efficient operation of the device.

While the invention has been described with reference to a surgical trephine device as the preferred embodiment, it is envisioned that the present invention will have broader application to non-surgical devices and methods for forming cylindrical or reverse tapered apertures in flexible material. In this respect, the present invention encompasses a trephine device for forming apertures in a flexible material of predetermined thickness, where the device includes an anvil 52 having a frusto-conical surface for engaging one side of the flexible material, a reciprocal clamping member 23 for engaging an opposite side of the flexible material from the anvil and for stretching the flexible material over the anvil into engagement with the frusto-conical surface of the anvil, and a reciprocal, cylindrical cutter 30 disposed coaxial with the anvil and having a cutting edge engagable with the flexible material held in a stretched condition by the clamping member for cutting through the flexible material to the anvil for forming an aperture through the flexible material. Preferably, the clamping member is moveable independently of the cutter. The frusto-conical surface of the anvil defines an axis and has an angle with respect to the axis selected to form a cylindrical aperture through the flexible material when the stretched material is cut with the cutter. By selecting an appropriate angle, the anvil and cutter can cooperate to produce an cylindrical aperture or a reverse tapered aperture through the flexible material when the material stretched over the anvil is cut with the cutter.

The present invention includes a method for forming an aperture through a flexible material of predetermined thickness including the steps of: operably engaging one side of the flexible material with an anvil having a frusto-conical surface; operably engaging an opposite side of the flexible material from the anvil with a moveable clamping member for stretching the flexible material over the anvil into engagement with the frusto-conical surface of the anvil; and moving a cylindrical cutter in coaxial relationship with the anvil, the cutter having a cutting edge engagable with the flexible material held in a stretched condition by the clamping member for cutting through the flexible material to the anvil thereby forming an aperture through the flexible material. The method can also include the step or steps of moving the clamping member independently of the cutter; and/or forming a circular aperture or reverse tapered aperture as the cutter passes through the flexible material stretched over the anvil. The method can include the step or steps of reciprocating the cutter when disposed coaxial with respect to the anvil; and/or rotating the cylindrical cutter about an axis coaxial with the anvil as the cutter passes through the flexible material stretched over the anvil.

While the invention has been described in connection with what is considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An apparatus for forming apertures in a flexible material of predetermined thickness, comprising:

an anvil having a frusto-conical surface operably engagable with one side of the flexible material;

a moveable clamping member operably engagable with an opposite side of the flexible material from the anvil for stretching the flexible material over the anvil into engagement with the frusto-conical surface of the anvil; and a cylindrical cutter moveable in coaxial relationship with the anvil and having a cutting edge engagable with the flexible material held in a stretched condition by the clamping member for cutting through the flexible material to the anvil for forming an aperture through the flexible material.

2. The apparatus of claim 1 further comprising:
   the clamping member moveable independently of the cutter.

3. The apparatus of claim 1 further comprising:
   the frusto-conical surface of the anvil defining an axis and having an angle with respect to the axis selected to form a cylindrical aperture through the flexible material when the stretched material is cut with the cutter.

4. The apparatus of claim 1 further comprising:
   the frusto-conical surface of the anvil defining an axis and having an angle with respect to the axis selected to form a reverse taper aperture through the flexible material when the stretched material is cut with the cutter.

5. A method for forming an aperture through flexible material of predetermined thickness comprising the steps of:

operably engaging one side of the flexible material with an anvil having a frusto-conical surface;

operably engaging an opposite side of the flexible material from the anvil with a moveable clamping member for stretching the flexible material over the anvil into engagement with the frusto-conical surface of the anvil; and moving a cylindrical cutter in coaxial relationship with the anvil, the cutter having a cutting edge engagable with the flexible material held in a stretched condition by the clamping member for cutting through the flexible material to the anvil thereby forming an aperture through the flexible material.

6. The method of claim 5 further comprising the step of:
   moving the clamping member independently of the cutter.

7. A trephine device for surgically preparing an aperture through skin of a patient comprising:

a base plate, the base plate having an upper surface and an opposed lower surface, the upper surface having at least one upwardly protruding skin deforming contour frusto-conical defined therein, the base plate adapted to be removably inserted into a pocket surgically prepared in tissue of the patient;

a handle member mounted on the base plate and projecting upwardly from the upper surface;

a skin clamping mechanism connected to the trephine device in overlying relationship to the upper surface of the base plate, the skin clamping mechanism including means for facilitating deformable, clamping, sandwiched engagement of the skin between the upper surface of the base plate and the skin clamping mechanism when the base plate is inserted into the pocket surgically prepared in the tissue of the patient; and a cutter mechanism positioned in the handle member, the cutter mechanism movable relative to the skin clamping mechanism into cutting engagement with the skin deformably engaged by the cutting mechanism.

8. The trephining device of claim 7 wherein the skin deforming means of the skin clamping mechanism comprises:

a circular deflection skin engaging unit composed of a tubular body having a hollow central interior aperture, the skin engaging unit constructed of a material capable of compressively deforming a layer of skin against the upwardly protruding contour defined in the underlying base plate.

9. The trephine device of claim 7 wherein the cutter means comprises:

a cutter blade having an cutting edge oriented toward the upper surface of the base plate;

means for telescopically extending and retracting the cutter blade relative to the handle member and associated skin engaging unit in a direction essentially perpendicular to the upper face of the base plate; and means for rotating the cutter blade coaxially about a center axis defined by the skin engaging unit.

10. The trephine device of claim 9 wherein the cutter blade is a tubular cutter element and the means for telescopically extending and retracting the cutter blade causes the cutter blade to move relative to and though the hollow interior aperture defined in the skin engaging unit.

11. The trephine device of claim 7 wherein the base plate comprises a generally elongate body having a first end and an opposed second end, the first end adapted to be received within a pocket surgically prepared in the skin tissue of a patient, the first end having outer peripheral contours essentially similar to contours of a permanent device to be implanted at the conclusion of a trephining procedure.

12. The trephine device of claim 11 wherein the base plate comprises:

a circular relief defined in the upper surface of the base plate at a location coaxial with of the cutter mechanism; and an anvil positioned coaxial to the circular relief.

13. The trephine device of claim 12 wherein the anvil comprises:

a head the element having a frusto-conical contour along an upper region;

a base integrally formed with the frusto-conical upper region, the head element having a cross-section containable within an area defined by the circular relief in the base plate; and wherein the anvil is positioned essentially coaxial to a forward axis defined in the base plate projecting from the base plate through the cutter mechanism.

14. The trephine device of claim 13 wherein the frusto-conical upper region of the head element of the anvil has an angle of taper sufficient to deform the skin layer when the skin layer is positioned in overlying relationship thereto.

15. The trephine device of claim 14 wherein the angle of taper of the upper region of the anvil is between about 20° and about 40°.

16. The trephine device of claim 13 wherein the base plate includes a hollow aperture defined in the upper surface at a location coaxial to the circular relief defined in the upper face and the anvil further comprises a rod formed integrally with and extending downwardly from the base of the anvil head element, the rod adapted to be matingly received within the hollow aperture defined in the base plate.

17. The trephine device of claim 7 wherein the handle member comprises:

a handle pedestal, the handle pedestal having an upper region and an opposed lower region, wherein the lower region of the handle pedestal contacts the upper face of the base plate, the handle pedestal projecting upward from the upper surface of the base plate;

means for releasibly mounting the handle pedestal to the base plate; and a hand grasp member integrally connected with the upper region of the handle pedestal.

18. The trephine device of claim 17 wherein the hand grasp member comprises:

a first arm portion, the first arm portion extending perpendicularly outward from the handle pedestal at an orientation essentially parallel to the base plate and terminating at a position in overlying relationship to the anvil, the first arm portion having a forward aperture defined therein adapted to facilitate retractable movement of the cutting mechanism relative to the first arm, the forward aperture extending through the first arm from top to bottom, the forward aperture located at a position essentially coaxial to the anvil and the forward axis located in base plate;

a second arm portion opposed to the first arm portion extending to a position beyond the end of the second region of base plate, the second arm portion having a rearward aperture defined therein;

clamp rod retractably positioned in the rearward aperture; and means for maintaining the clamp rod in a clamped position.

19. The trephine device of claim 18 wherein the position retaining means comprises:

a clamp rod having an upper end and a lower end, the lower end projecting through the lower portion of the rearward aperture in the second arm of the handle pedestal;

a knob located proximate to the upper end of clamp rod;

a cross pin located proximate to the lower end of the clamp rod; and biasing means compressively positioned between the upper surface of the handle member and the clamp rod.

20. The trephine device of claim 7 wherein the skin clamping mechanism comprises:

a skin engaging unit; and a clamp arm pivotally mounted on the handle member, the clamp having a central body connected to the handle member, the central body having a first end and a second end opposed to the first end, the clamp further having a fork member extending contiguously from the first end, the fork member composed of two arms adapted to receive and pivotally engage the skin engaging unit.

* * * * *